(12) United States Patent
Bush

(10) Patent No.: US 10,772,534 B2
(45) Date of Patent: Sep. 15, 2020

(54) SINGLE-POINT GASTRIC EMPTYING BREATH TESTS

(71) Applicant: Advanced Breath Diagnostics, LLC, Brentwood, TN (US)

(72) Inventor: Kerry C. Bush, Brentwood, TN (US)

(73) Assignee: ADVANCED BREATH DIAGNOSTICS, LLC, Brentwood, TN (US)

( * ) Notice: Subject to any disclaimer, the term of this patent is extended or adjusted under 35 U.S.C. 154(b) by 907 days.

(21) Appl. No.: 13/798,341

(22) Filed: Mar. 13, 2013

(65) Prior Publication Data

US 2014/0276172 A1    Sep. 18, 2014

(51) Int. Cl.
A61B 5/083      (2006.01)
A61B 6/00       (2006.01)
A61K 51/12      (2006.01)
A61K 49/00      (2006.01)

(52) U.S. Cl.
CPC .............. *A61B 5/0836* (2013.01); *A61B 6/00* (2013.01); *A61K 49/0004* (2013.01); *A61K 51/1296* (2013.01)

(58) Field of Classification Search
CPC ................... A61B 5/0836; A61B 5/08; A61B 5/083–0836; A61B 6/00; A61K 49/00; A61K 49/0004; A61K 51/1293; A61K 51/1296
See application file for complete search history.

(56) References Cited

U.S. PATENT DOCUMENTS

| | | | |
|---|---|---|---|
| 4,985,232 A | 1/1991 | Jacobssen |
| 5,140,993 A | 8/1992 | Opekun |
| 5,233,997 A | 8/1993 | Klein |
| 5,707,602 A | 1/1998 | Klein |
| 5,785,949 A | 7/1998 | Klein |
| 6,273,854 B1 | 8/2001 | Kane |
| 6,432,382 B1 | 8/2002 | Mehta |
| 6,548,043 B1 | 4/2003 | Wagner |
| 6,740,305 B1 | 5/2004 | Ajami |
| RE38,728 E | 4/2005 | Katzman |
| 7,141,016 B2 | 11/2006 | Lyke |
| 7,785,569 B2 | 8/2010 | Evans |
| 2002/0011250 A1 | 1/2002 | Stewart |
| 2003/0211042 A1 | 11/2003 | Evans |

(Continued)

FOREIGN PATENT DOCUMENTS

| | | | |
|---|---|---|---|
| EP | 1624902 B1 | 1/2009 |
| EP | 1503805 B1 | 11/2011 |

(Continued)

OTHER PUBLICATIONS

"Single time point diagnostic breath tests: a review" by Modak, Journal of Breath Research, vol. 4, pp. 1-6, 2010.*

(Continued)

*Primary Examiner* — Jacqueline Cheng
*Assistant Examiner* — Jairo H Portillo
(74) *Attorney, Agent, or Firm* — Fredrikson & Byron, P.A.

(57) ABSTRACT

A gastric emptying breath test method that includes collecting a breath sample of the subject at only a single time point after the subject consumes the breath test meal, wherein the single time point is a time point selected from within an identified time window.

11 Claims, 6 Drawing Sheets

Relationship of GEBT and Scintigraphic Measurements, r = 0.84

(56) References Cited

U.S. PATENT DOCUMENTS

| | | | |
|---|---|---|---|
| 2004/0062711 A1* | 4/2004 | Meier-Augenstein | ................... A61K 51/1206 424/9.1 |
| 2006/0074335 A1* | 4/2006 | Ben-Oren | ............. A61B 5/083 600/532 |
| 2007/0014718 A1 | 1/2007 | Lee | |
| 2008/0033253 A1 | 2/2008 | Neville | |
| 2008/0075658 A1 | 3/2008 | Burke | |
| 2008/0281166 A1* | 11/2008 | Bush | ................... A61B 5/0836 600/300 |
| 2008/0281193 A1 | 11/2008 | Oren | |
| 2008/0281194 A1 | 11/2008 | Bush | |
| 2008/0286200 A1 | 11/2008 | Bush | |
| 2010/0241606 A9 | 9/2010 | Wanger | |
| 2011/0223104 A1 | 9/2011 | Bush | |

FOREIGN PATENT DOCUMENTS

| | | |
|---|---|---|
| GB | 2360845 | 10/2001 |
| WO | 9735622 | 10/1997 |
| WO | 0172342 | 10/2001 |
| WO | 2009152222 A1 | 12/2009 |

OTHER PUBLICATIONS

Mccallum, Richard W., David M. Berkowitz, and Emanuel Lerner. "Gastric emptying in patients with gastroesophageal reflux." Gastroenterology 80.2 (1981): 285-291. (Year: 1981).*

PCT International Search Report and Written Opinion dated Jun. 10, 2014 for related Intl. Application No. PCT/US2014/023921, 10 pgs.

J S Lee, et al., "A Valid, Accurate, Office Based Non-Radioactive Test for Gastric Emptying of Solids," Gut 2000; 46:768-773.

B.E. Viramontes, et al., "Validation of a Stable Isotope Gastric Emptying Test for Normal, Accelerated or Delayed Gastric Emptying," Neurogastroenterol. Mot. (2001) 13, 567-574.

Yvo F. Ghoos, et al., "Measurement of Gastric Emptying Rate of Solids by Means of a Carbon-Labeled Octanoic Acid Breath Test," Gastroenterology 1993;104:1640-1647.

Abell et al., "Treatment of gastroparesis: a multidisciplinary clinical review", Neurogastroenterol Motil (2006) 18, 263-283.

B. Rosner, On the Detection of Many Outliers, Technometrics, 17/2, 221-227 (1975).

Breidthardt et al., "Medical and Economic Long-term Effects of B-type Natriuretic Peptide Testing in Patients with Acute Dyspnea", Clinical Chemistry 53:8 (2007), 1415-1422 .

Bytzer et al., "Gastrointestinal symptoms in Diabetes Mellitus are Associated with Diabetic Complications but not with Current Glycemic Control," Abstract from Digestive Disease Week (DDW) 2000; Gastroenterology 2000; 118:A468.

Bytzer et al., "GI Symptoms in Diabetes Mellitus are Associated with Both Poor Glycemic Control and Diabetic Complications" Am J Gastroenterology; 2002, vol. 97, No. 3, pp. 604-611.

Bytzer et al., "Prevalence of gastrointestinal symptoms associated with diabetes mellitus: a population-based survey of 15,000 adults," Arch Intern Med 2001; 161:1989-1996.

Chamorro et al., "Pharmacology and toxicology of spirulina alga," Rev Invest Clin Sep.-Oct. 1996; 48(5):389-99.

Chamorro et al., "Subchronic toxicity study in rats fed spirulina," J. Pharm Belg., 1988, 43, 1, 29-36.

Ciferri et al., "Spirulina the Edible Microorganism," Microbiological Reviews, Dec. 1983, p. 551-578.

Coste et al., "A Gray Zone Assigned to Inconclusive Results of Quantitative Diagnostic Tests: Application to the Use of Brain Natriuretic Peptide for Diagnosis of Heart Failure in Acute Dyspneic Patients", Clinical Chemistry 52:12 (2006), 2229-2235.

Enck et al., "Prevalence of gastrointestinal symptoms in diabetic patients and non-diabetic subjects," Z Gastroenterol 1994; 32:637-641.

FDA Talk Paper, "Spirulina", Jun. 23, 1981.

Feinstein, "The inadequacy of binary models for the clinical reality of three-zone diagnostic decisions", J Clin Epidemiol, 43, 109-113 (1990).

Harris, et al., Statistical Bases of Reference Values in Laboratory Medicine, Marcel Dekker, 1995, Chapter 8: Analytical Goals for Reference Values.

Janatuinen et al., "Gastrointestinal symptoms in middle-aged diabetic patients," Scan J Gastroenterol 1993; 28:427-432.

Krishnakumari et al., "Food safety evaluation: acute oral and dermal effects of the algae scenedesmus acutus and spirulina platensis on albino rats", J. of Food Protection, vol. 44, No. 12, Dec. 1981, 934-935.

Lidums et al., "Effect of atropine on proximal gastric motor and sensory function in normal subjects", Gut 2000; 47:30-6.

Maleki et al., "Gastrointestinal tracts symptoms among persons with diabetes mellitus in the community," Arch Intern Med 2000; 160:2808-2816.

Park et al., "Clinical Reviews: Gastroparesis: Clinical Update" American Journal of Gastroenterology, ISSN 0002-9270 (2006), 1129-1139.

R.S. Chhikara et al, Extended critical Values of Extreme Studentized Deviate Test Statistics for Detecting Multiple Outliers, Commun. Statist.-Simula. Computa., B9(2), 155-166 (1980).

Salazar et al., "Effect of spirulina maxima consumption on reproduction and peri- and postnatal development in rats," Food and Chemical Toxicology, 34 (1996) 353-359.

Schofield, "Predicting basal metabolic rate, new standards and review of previous work", Hum Nutr Clin Nutr (1985) 39, 541.

Solberg, "RefVal: a program implementing the recommendations of the International Federation of Clinical Chemistry on the statistical treatment of reference values", Computer Methods and Programs in Biomedicine 1995, 48:247-256.

Szarka et al. "A Stable Isotope Breath Test with a Standard Meal for Abnormal Gastric Emptying of Solids in the Clinic and in Research", Clinical Gastroenterology and Hepatology, 2008; 6:635-643.

Talley et al., "Effects of a motilin receptor agonist (ABT-229) on upper gastrointestinal symptoms in type 1 diabetes mellitus: a randomized, double-blind, placebo controlled trial," Gut 2001; 49:395-401.

Talley et al., "Epidemiology of colonic symptoms and the irritable bowel syndrome," Gastroenterology 101:927-934, 1991.

Taub et al, "Irritable bowel syndrome defined by factor analysis. Gender and race comparisons." Dig Dis Sci 40:2647-2655, 1995.

Yoshino et al., "The chronic intoxication test of spirulina product fed to wistar rats," Japanese Journal of Nutrition, 38 (5), 1980, 221-226.

Zuckerman et al. "Healthcare-seeking behaviors related to bowel complaints. Hispanics versus non-Hispanic whites." Dig Dis Sci 41:77-82, 1996.

Bouras et al., "Gastric Motility disorders: Management that Optimizes Nutritional status," Journal of Clinical Gastroenterology 38(7):549 (2004).

Pellegrini et al., "Diagnosis and Treatment of Gastric Emptying Disorders," American Journal of Surgery 145:143 (1983).

Bjorkman et al., The Am. J. of ., Gasteroenterology 86 (7) : 821-823 (1991).

Choi et al. Gasteroenterology 112(4) : 1155-1162 (1997)—Absract Only—Online.

Donohoe et al., J. of Nuc. Med. 40(7) : 1236-1239 (1999).

Ducrot et al. Digestive Diseases and Sciences 34 (5) : 657-664 (1989).

Symonds et al, J. Nutr. 134: 1193-1196, 2004.

Bratten et al, Digestive Diseases, 2006, 24:252-259.

Braden et al, Best Practice and Research Clinical Gastroenterology, 2009, 23:337-352.

Szarka et al, Am. J. Physiol. Gastrointest. Liver Physiol., 2009, 296:G461-G475.

Graham et al, American J. Gastroenterology, 2001, 96/6:1741-1745.

Geypens et al, J. Nucl. Med., 1999, 40:1451-1455.

Braden et al, Digestive and Liver Disease 39 (2007) 795-805.

(56) References Cited

OTHER PUBLICATIONS

Abell et al., "Consensus Recommendations for Gastric Emptying Scintigraphy: A Joint Report of the American Neurogastroenterology and Motility Society and the Society of Nuclear Medicine," American Journal of Gastroenterology 2008, 103: 753-763.

\* cited by examiner

Figure 1: Mean Breath Test Values of Normal vs. Delayed Subjects with 95% Confidence Intervals
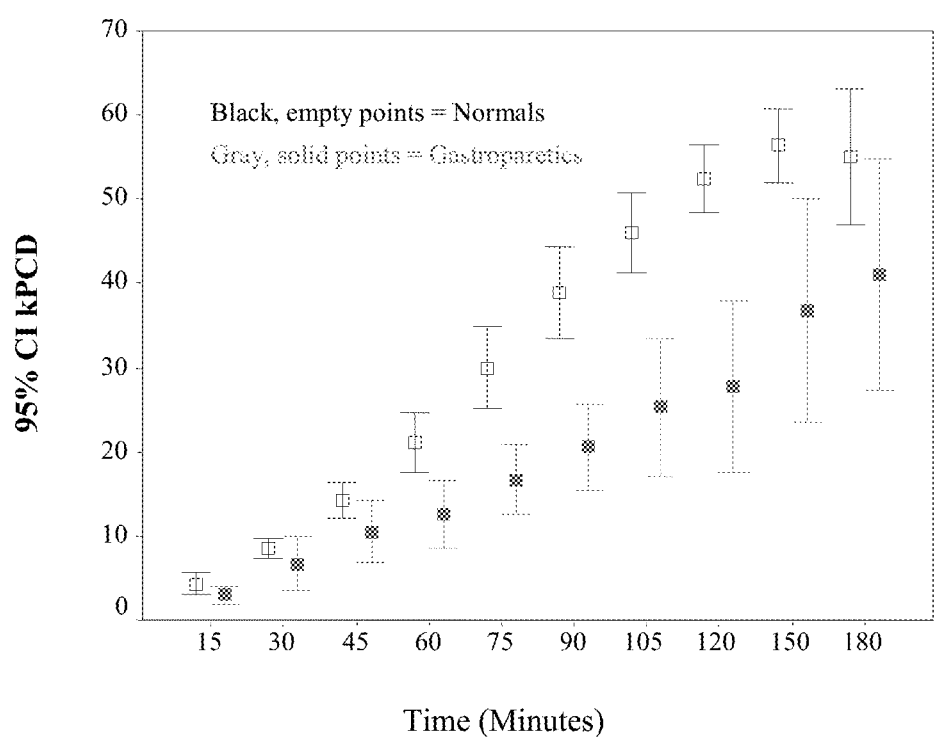

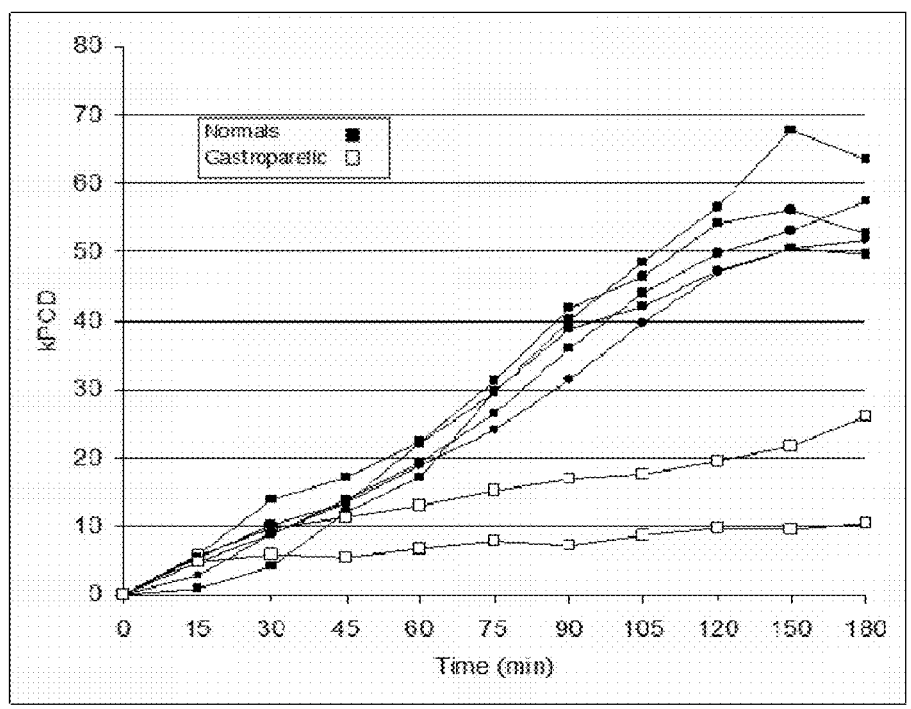
Figure 2: Normal vs. Delayed Subjects

Figure 3: Percent of Test Meal Retained Over Time - Scintigraphy
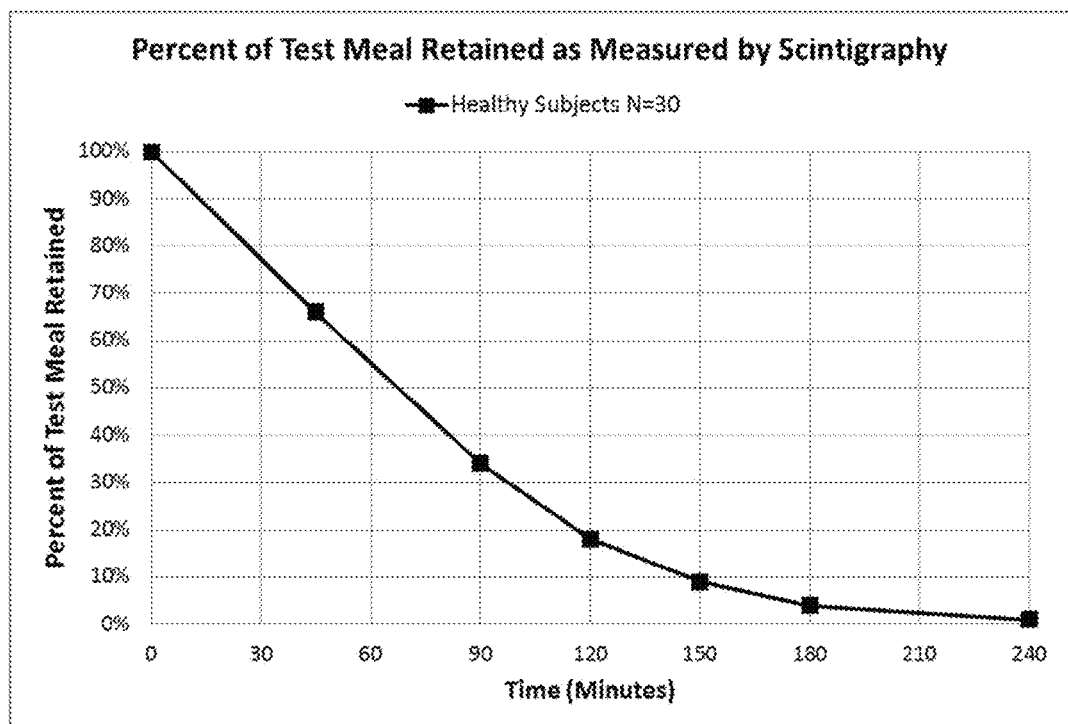

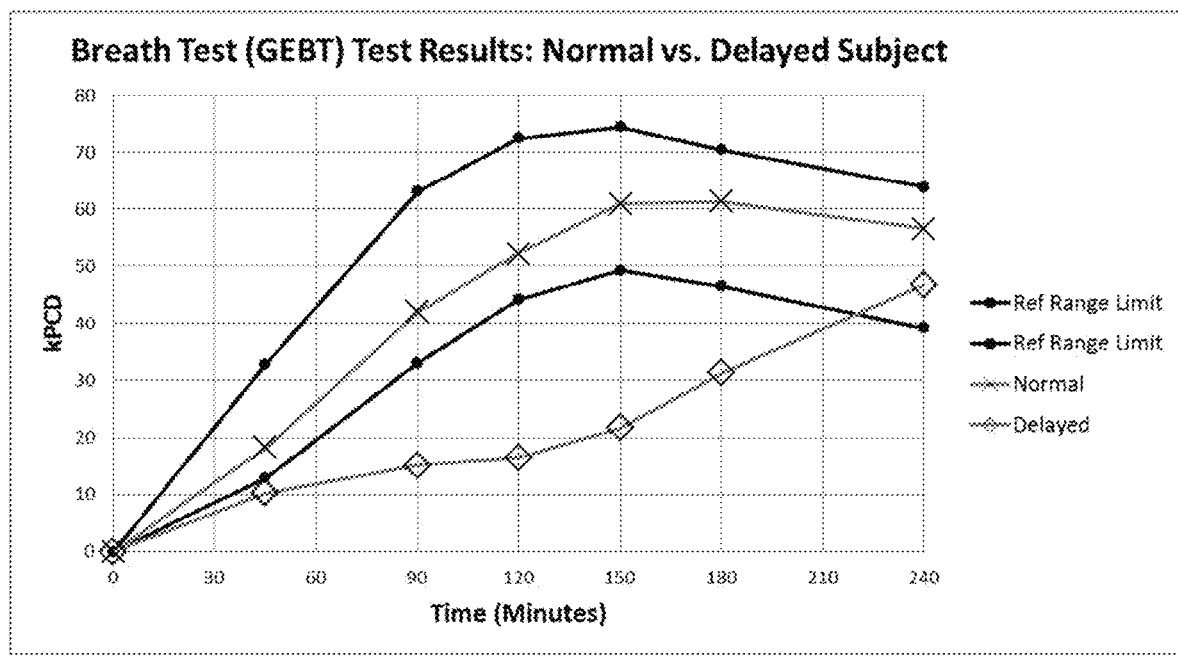
Figure 4: Normal vs. Delayed Subject

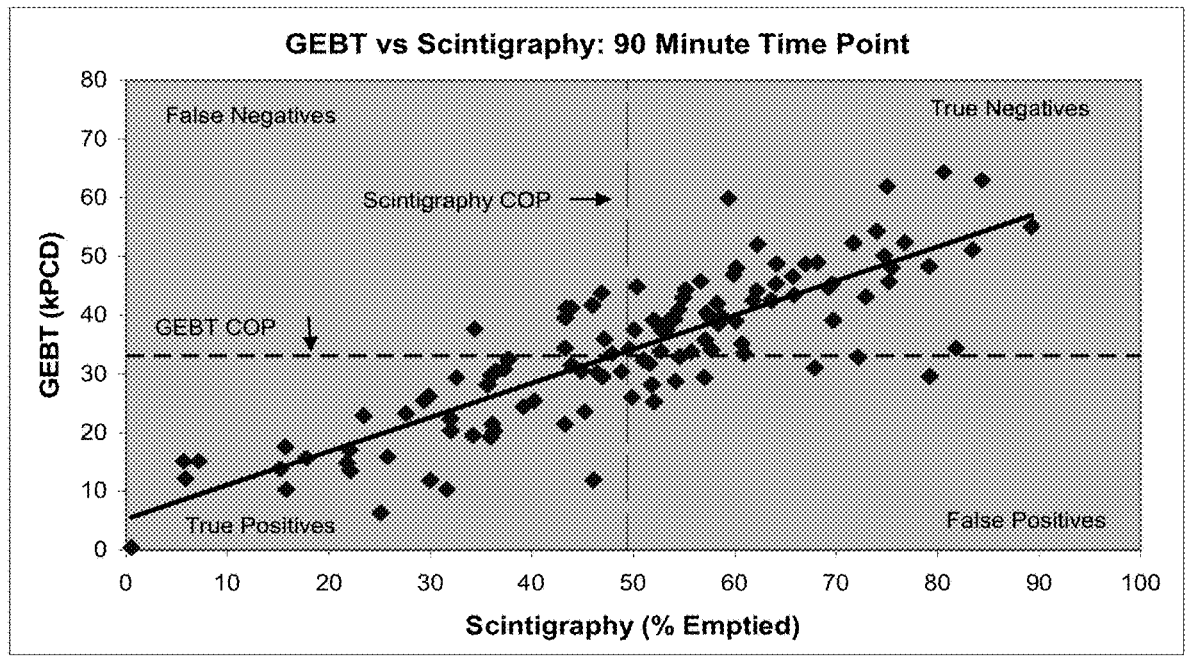
Figure 5: Relationship of GEBT and Scintigraphic Measurements, r = 0.84

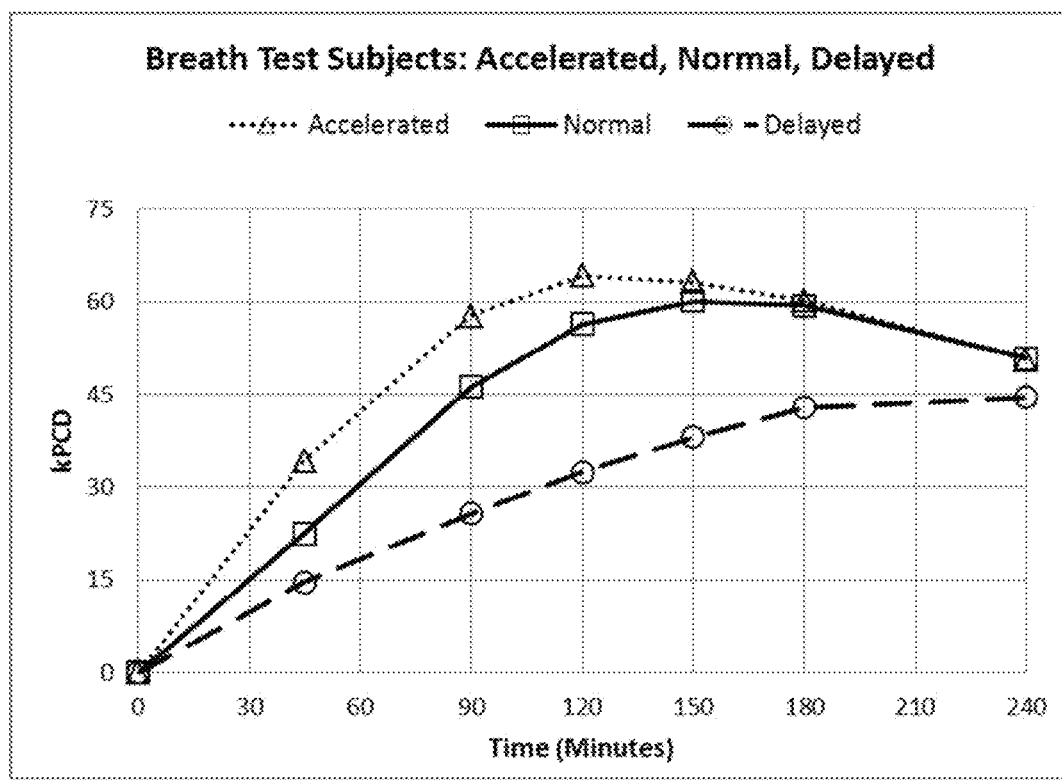
Figure 6: Normal vs. Accelerated Subjects

SINGLE-POINT GASTRIC EMPTYING BREATH TESTS

FIELD

The present invention generally relates to gastric emptying breath tests.

BACKGROUND

The digestive tract generally performs five functions when processing food. The functions include motility, secretory, digestive absorptive and elimination functions. Food processing begins in the oral cavity, which mechanically breaks down food by mastication, lubrication with saliva, and enzymatic processing. Food processing continues in the stomach where food is liquefied by gastric juices and enzymes secreted by the cells lining the stomach to produce chyme. The chyme next enters the small intestine where bile salts produced by the liver and digestive enzymes produced by the pancreas further process the chyme. The small intestine also absorbs components from the chyme through its walls. Components that are not absorbed by the small intestine enter the large intestine. Finally, the large intestine propels waste products into the colon, where they remain, usually for a day or two, until the feces are expelled by a bowel movement.

Sometimes, a person takes an abnormally long time to process food, or a person processes food abnormally fast. Such abnormal gastrointestinal functions are commonly caused by a disorder in the stomach. A stomach disorder can cause the stomach to empty food into the small intestine too quickly or after too long of a time. Stomach emptying disorders can be diagnosed by measuring the rate at which a meal empties from the stomach and enters the small intestine (the "gastric emptying rate"). When the rate is accelerated, the stomach prematurely dumps food into the small intestine, giving rise to abnormally fast rates of gastric emptying (rapid or accelerated gastric emptying). Conversely, when the rate is delayed, the stomach delays moving food into the small intestine, giving rise to abnormally slow rates of gastric emptying (delayed gastric emptying). Hence, measurements of gastric emptying rates have important clinical utility.

Various methods are known for quantitatively measuring gastric emptying rates. One known method is scintigraphy, which has historically been considered the gold standard method of measuring gastric emptying rates. In a scintigraphy method, a subject ingests a meal including at least one edible food, a component of which has been radiolabeled with a gamma emitting radionuclide. A scintillation camera or gamma counter scans the stomach at different time points over an extended time period. The scans directly measure the gamma emissions arising from the radiolabeled meal remaining in the stomach.

Two metrics are commonly utilized in scintigraphy methods. These are (1) fraction of test meal emptied at a number of different time points and (2) the time it takes to empty 50% of a standard test meal from the stomach, or "t ½." A scintigraphic t ½ value for a test subject may be obtained from using the fraction emptied values by linear interpolation between the two time points at which scintigraphic fraction emptied values bracket 0.5 (50% emptied). Thus, scintigraphy methods use metrics that require taking measurements at a number of different time points.

Another method for measuring gastric emptying is breath testing. In a breath testing method, a subject ingests a meal including at least one edible food, a component that includes a $^{13}C$ label. As the subject's digestive tract processes the $^{13}C$ labeled food, a labeled digestive metabolite, $^{13}CO_2$, is produced which can be detected in the subject's breath. The $^{13}C$ label passes through the stomach, is absorbed by the small intestine and is metabolized by the liver to give rise to $^{13}CO_2$. The $^{13}CO_2$ then moves through the blood to the lungs and exits the body through the subject's breath. The rate of excretion of $^{13}CO_2$ in the breath signals the rate at which the stomach is emptying. During breath testing, a test administrator collects breath samples from a subject at a number of different time points. Thus, breath testing also requires taking measurements at a number of different time points.

Both scintigraphy and breath testing methods are multipoint tests. Following consumption of a meal including the label, successive measurements are obtained at multiple time points, for example at time points at selected intervals for up to six hours. Such test methods therefore are inconvenient because they require taking measurements at multiple time points and require a long period of time to complete.

SUMMARY

In some embodiments, the invention provides a breath test method for diagnosing delayed gastric emptying. The method includes the steps of supplying a subject with a breath test meal having a $^{13}C$ label, collecting a breath sample of the subject at only a single time point after the subject consumes the breath test meal, wherein the single time point is a time point selected from within the time window of between about 90 minutes and about 150 minutes, generating a gastric emptying measurement from the breath sample and using the measurement to provide a test result. In some cases, the single time point is a 90 minute time point.

In other embodiments, the invention provides a breath test method for diagnosing rapid gastric emptying. The method includes the steps of supplying a subject with a breath test meal having a $^{13}C$ label, collecting a breath sample of the subject at only a single time point after the subject consumes the breath test meal, wherein the single time point is a time point selected from within the time window of between about 30 minutes and about 90 minutes, generating a gastric emptying measurement from the breath sample, and using the measurement to provide a test result.

In other embodiments, the invention provides a gastric emptying breath test method that includes the steps of supplying a subject with a breath test meal having a $^{13}C$ label, collecting a breath sample of the subject at only a single time point after the subject consumes the breath test meal, wherein the single time point is a time point has been previously validated as showing a selected measurement difference between breath test measurements for normal subjects and breath test measurements for abnormal subjects, generating a gastric emptying measurement from the breath sample and using the measurement to provide a test result. In some cases, the abnormal subjects are subjects who have previously obtained a delayed gastric emptying test result and the selected measurement difference is a measurement difference of at least 10 kPCD between normal subjects and delayed subjects. In other cases, the abnormal subjects are subjects who have previously obtained an accelerated gastric emptying test result and the selected measurement difference is a measurement difference of at least 10 kPCD between normal subjects and accelerated subjects.

In other embodiments, the invention provides a gastric emptying breath test method that includes the steps of supplying a subject with a breath test meal, collecting a breath sample of the subject at only a single time point after the subject consumes the breath test meal, and generating a breath test result from the breath sample, wherein the single time point is a time point that meets at least one of the following criteria (a) through (e):
(a) the diagnostic sensitivity of the breath test method at the single time point is at least 75% as compared to a scintigraphy method when using the same breath test meal for both test methods;
(b) the diagnostic specificity of the breath test method at the single time point is at least 75% as compared to a scintigraphy method when using the same breath test meal for both test methods;
(c) the overall diagnostic concordance of the breath test method at the single time point is at least 75% as compared to a scintigraphy method when using the same breath test meal for both test methods;
(d) the Positive Predictive Value (PPV) of the breath test method at the single time point is at least 75% as compared to a scintigraphy method when using the same breath test meal for both test methods; and
(e) the Negative Predictive Value (NPV) of the breath test method at the single time point is at least 75% as compared to a scintigraphy method when using the same breath test meal for both test methods I.

In each of these breath test methods, the breath test meal can have a $^{13}C$ label (e.g., a $^{13}C$-*Spirulina platensis* label) in a sufficient dose (e.g., a dose of between about 20 mg to about 80 mg) that statistically discriminates between normal subjects and delayed subjects or between normal subjects and accelerated subjects. The breath test meal can also have a caloric content of between about and about 200 and about 400 kCal.

In other embodiments, the invention provides a method for developing a single-point breath test that includes the steps of performing gastric emptying breath tests on a series of normal subjects to obtain breath test measurements at a series of time points, performing gastric emptying breath tests on a series of abnormal subjects to obtain breath test measurements at the series of time points, and selecting a single time point from the series of time points that shows a selected measurement difference between breath test measurements for normal subjects and breath test measurements for abnormal subjects. In some cases, the abnormal subjects are subjects who have previously obtained a delayed gastric emptying test result and the selected measurement difference is a measurement difference of at least 10 kPCD between normal subjects and delayed subjects. In other cases, the abnormal subjects are subjects who have previously obtained an accelerated gastric emptying test result and the selected measurement difference is a measurement difference of at least 10 kPCD between normal subjects and accelerated subjects.

In other embodiments, the invention provides a method for developing a single-point breath test that includes the steps of performing gastric emptying breath tests on a series of normal subjects to obtain breath test measurements at a series of time points, performing gastric emptying breath tests on a series of abnormal subjects to obtain breath test measurements at the series of time points, selecting a single time point from the series of time points that shows any measurement different between normal subjects and abnormal subjects, calculating a 95% confidence interval around a mean value of the normal subjects at the selected single time point, calculating a 95% confidence interval around a mean value of the abnormal subjects at the selected single time point, and using the selected single time point in a single-point breath test if the 95% confidence interval around the mean value of the normal subjects does not overlap with the 95% confidence interval around the mean value of the abnormal subjects. In some cases, the abnormal subjects are subjects who have previously obtained a delayed gastric emptying test result or subjects who have previously obtained an accelerated gastric emptying test result. The step of selecting a single time point from the series of time points that shows any measurement different between normal subjects and abnormal subjects can be a step of selecting a single time point from the series of time points that shows a measurement difference of at least 10 kPCD.

In other embodiments, the invention provides a method for selecting a time point for a single-point breath test. The method includes the steps of performing both a gastric emptying breath test and a scintigraphy test on a series of normal subjects to obtain both breath test measurements and scintigraphy measurements at a series of time points, performing both a gastric emptying breath test and a scintigraphy test on a series of abnormal subjects to obtain both breath test measurements and scintigraphy measurements at a series of time points, calculating a diagnostic sensitivity of the breath test measurement compared to the scintigraphy measurements at a time point from the series of time points, and selecting the time point for a single-point breath test if the time point has a diagnostic sensitivity of at least 75%.

In other embodiments, the invention provides a method for selecting a time point for a single-point breath test. The method includes the steps of performing both a gastric emptying breath test and a scintigraphy test on a series of normal subjects to obtain both breath test measurements and scintigraphy measurements at a series of time points, performing both a gastric emptying breath test and a scintigraphy test on a series of abnormal subjects to obtain both breath test measurements and scintigraphy measurements at a series of time points, calculating a diagnostic sensitivity of the breath test measurement compared to the scintigraphy measurements at a time point from the series of time points, and selecting the time point for a single-point breath test if the time point has a diagnostic specificity of at least 75%.

BRIEF DESCRIPTION OF THE DRAWINGS

The following drawings are illustrative of particular embodiments of the invention and therefore do not limit the scope of the invention. The drawings are not to scale (unless so stated) and are intended for use in conjunction with the explanations in the following detailed description. Embodiments of the invention will hereinafter be described in conjunction with the appended drawings, wherein like numerals denote like elements.

FIG. 1 is a graph of the average breath test kPCD values for normal versus delayed subjects over time using a 20 mg $^{13}C$ dose.

FIG. 2 is a graph of breath test kPCD values for normal and delayed subjects over time using a 43 mg $^{13}C$ test meal.

FIG. 3 is a plot of the fraction (%) of test meal retained in the stomach of healthy subjects over time as measured by scintigraphy.

FIG. 4 is a graph of kPCD values for a normal and a delayed subject over time.

FIG. 5 is a scatter plot of breath test versus scintigraphic measurements for a group of subjects at 90 minutes.

FIG. 6 is a graph of breath test kPCD values for normal and accelerated subjects over time.

DETAILED DESCRIPTION

For the purpose of promoting an understanding of the principles of the invention, reference will now be made to the embodiments illustrated in the drawing and specific language will be used to describe the same. It will, nevertheless, be understood that no limitation of the scope of the invention is thereby intended; any alterations and further modifications of the described or illustrated embodiments, and any further applications of the principles of the invention as illustrated therein, are contemplated as would normally occur to one skilled in the art to which the invention relates.

The invention includes breath test methods that can detect and diagnose delayed gastric emptying or rapid gastric emptying by obtaining breath sample(s) at a single time point that occurs during a special time window. Applicant has discovered that a maximum difference in gastric emptying between normal and delayed subjects (or between normal and accelerated subjects) occurs during a special time window, and this difference is of a sufficient magnitude to allow for diagnosing of delayed gastric emptying (or rapid gastric emptying) by obtaining breath samples from a single time point within that time window only. As a result, it is not necessary to take measurements at multiple time points or to continue breath testing for a prolonged period of time in order to diagnose delayed gastric emptying (or rapid gastric emptying). Rather, measurements taken at a single time point during this time window can alone be used to diagnose delayed gastric emptying (or rapid gastric emptying).

The single-point breath test is advantageous over multi-point tests because it is quicker, easier to administer and is less expensive than multi-point tests. A single-point breath test can also be used on a more widespread basis. For example, multi-point tests typically need to be administered in a tertiary referral center such as a nuclear medicine facility, a GI motility evaluation center or a hospital setting and require a longer period of time. On the other hand, the single-point breath test can quickly be administered during routine physicals to routinely screen subjects for digestive disorders.

The single-point breath test method is generally a method wherein breath sample(s) are taken at a single time point within a special time window after a subject ingests a meal. One exemplary single-point breath test method will now be described. A subject preferably fasts using any acceptable fasting protocol for a period of time before the test is administered. Before the breath test method is performed, a test administrator collects baseline breath samples from the subject. The subject then ingests a test meal that includes a $^{13}$C label incorporated into the meal. In some cases, the breath test meal has a caloric content of between about 200 and about 400 kCal. The subject consumes the meal in a single setting, for example within a specific time frame. The test administrator then collects one or more breath samples from the subject only at a single time point after the subject ingests the meal. The test administrator generates a gastric emptying measurement from the one or more breath samples and uses the measurement to provide a test result.

It should be understood that the single time point is the only time point breath samples are taken at. In some cases, only one breath sample is taken at the single time point. In other cases, multiple breath samples are taken at the single time point. For example, it may be desirable to obtain multiple breath samples at the single time point and then to provide a value that is the mean of the measurement generated from each sample. When multiple breath samples are obtained, the breath samples may be obtained consecutively, at approximately the same single time point, with the understanding that more than one sample cannot be obtained at exactly the same time. For example, there may be a delay of approximately 30 seconds or less between consecutive breath samples, such as approximately 15 seconds or less, and such samples may be considered to be collected at the same time point.

Further, the single-point breath test uses a single time point that falls within a special time window. Applicant has discovered a special time window during which a test administer can connect breath samples at a single time point. Applicant has determined the time window and/or the single time point within the time window by comparing gastric emptying rates of normal subjects and subjects affected with delayed gastric emptying (and of normal subjects and subjects affected with rapid gastric emptying).

In cases where the breath test is used for diagnosing delayed gastric emptying, the single time point falls within a time window of between about 90 minutes and about 150 minutes after the subject ingests the test meal. In some cases, the single time point for detecting delayed gastric emptying is a 90 minute single time point, 100 minute single time point, 110 minute single time point, 120 minute single time point, 130 minute time point, 140 minute time point, 150 minute time point, and any other time point in between these.

In cases where the breath test is used for diagnosing rapid gastric emptying, the single time point falls in a time window of between about 30 minutes and about 90 minutes after the subject ingests the test meal. In some cases, the single time point for detecting rapid gastric emptying is 30 minute time point, 35 minute time point, 40 minute time point, 45 minute time point, 50 minute time point, 55 minute time point, 60 minute time point, 65 minute time point, 70 minute time point, 75 minute time point, 80 minute time point, 85 minute time point, 90 minute time point and any other time point in between these.

The test meal includes a $^{13}$C label that is incorporated into the meal. In certain cases, a $^{13}$C label is incorporated into biomass, which is then incorporated into the test meal. For example, in specific cases, the test meal includes a $^{13}$C label incorporated into *Spirulina platensis*. *Spirulina platensis* labeled with $^{13}$C can be obtained by growing the algal cells in a $^{13}$C-enriched environment as is disclosed in commonly assigned U.S. Pat. No. 6,872,516, the disclosure of which is herein incorporated by reference in its entirety.

The test meal includes a $^{13}$C label at a dose that provides an excellent signal for single-point breath testing. In some cases, the dose is between about 20 mg and about 80 mg of $^{13}$C label or perhaps between about 40 mg and about 50 mg, such as 43 mg of $^{13}$C. In certain cases, the subject ingests $^{13}$C-*Spirulina platensis* at a dose of approximately 100 mg, which contains approximately 43 mg of $^{13}$C.

The $^{13}$C-*Spirulina platensis* is also incorporated into an edible food component that forms part of the test meal. The test meal includes any number of edible food components that can be ingested at a single setting. A single setting can be a designated time period, perhaps a period of less than 30 minutes, 20 minutes, or even 10 minutes. In many cases, the test meal can include a main food component as well as any side components and/or liquid components. In certain cases, the test meal includes food components derived from standardized, freeze-dried or lyophilized food components, such as those described in U.S. patent application Ser. No. 10/435,092, the entire contents of which are incorporated herein by reference.

In one particular embodiment, the test meal includes reconstituted lyophilized whole eggs and $^{13}$C-*Spirulina platensis* as a main food component. The $^{13}$C-*Spirulina platensis* in this embodiment is present in an amount of 100 mg. (which contains approximately 43 mg of $^{13}$C). The test meal can also include bread or crackers as a side component and/or milk or water as a liquid component.

The subject deposits a breath sample by blowing through a straw into the bottom of a glass tube to displace contained air and capture a clean breath sample. The test administrator caps the tube and then obtains the $^{13}CO_2$ content measurement of the breath for the tube using a mass spectrometer, infrared spectrometer or any other known instrument for measuring of $^{13}CO_2/^{12}CO_2$ ratios in breath.

The single time point measurement can be expressed using any metric known in the art. In certain cases, the measurement is expressed as kPCD and CumPCD. The PCD metric is the Percent Dose (abbreviated PCD) of $^{13}$C excreted at time t (in this case, at the single time point) after consumption of the test meal. To provide a more convenient scale, PCD is multiplied by 1000 to produce kPCD at time t. The kPCD can be calculated as follows:

$$kPCD_t = \left[ \frac{DOB * CO_2PR * R_s * 13}{10 * \text{dose}} \right] * 1000$$

where:
DOB=The measured difference in the $^{13}CO2/^{12}CO2$ ratio between the single time point measurement and the baseline measurement.
$CO_2PR=CO_2$ production rate (mmol $CO_2$/min) calculated using the Scholfield equations. The Scholfield equations are a set of equations which are fitted to people depending on their age, gender, height, and weight to estimate the basal metabolic rate (BMR), which is intimately related to $^{13}CO_2$ production rate. The equations are known in the art and allow the calculation of a specific $CO_2$ production rate for the individual being tested.
$R_s$=0.0112372, the ratio $[^{13}CO_2/^{12}CO_2]$ in an international reference standard (Pee Dee Belemite).
13=The atomic weight of $^{13}$C.
10=A constant factor for converting units.
Dose=The weight (mg) of $^{13}$C in the dose of $^{13}$C-*Spirulina platensis* administered to the subject in the test meal. For example, since $^{13}$C-*Spirulina platensis* is approximately 43% by weight $^{13}$C, a dose of 100 mg corresponds to approximately 43 mg of $^{13}$C.

The kPCD may be calculated for the single time point. In some embodiments, the $^{13}CO_2/^{12}CO_2$ ratios may be used to calculate the $^{13}CO_2$ excretion rate at the single time point. The measured $^{13}CO_2/^{12}CO_2$ ratio, the calculated $^{13}CO_2$ excretion rate, and/or the kPCD at the single time point can then be classified as normal v. delayed or as normal v. accelerated, using known classification methods in the art.

In some embodiments, a breath test measurement is considered normal at the single time point if it falls within a reference range. For example, if the single time point is a 90 minute time point, the measurement can be considered normal if it is between a 33.1 and 63.2 kPCD range and can be considered delayed if it is below this range. Similarly, if the single time point is a 120 minute time point, the measurement can be considered normal if it is between a 44.2 and 72.5 kPCD range and can be considered delayed if it is below this range.

In certain cases, the measurement can be considered normal if it is less than a cut-off point value for the single time point and abnormal if it is greater than a cut-off point value for the same single time point. For example, the cut-off point can be determined statistically using gastric emptying data from normal subjects. For instance, a cohort of normal, healthy subjects can be administered a specific standardized test meal containing either a $^{13}$C label for breath testing or a radionuclide label (i.e. $^{99m}$Tc sulfur colloid) for scintigraphy. Each healthy subject in the cohort is tested by the selected method of measuring gastric emptying. Measurements for each subject are collected at the single time point and then are arrayed. From this array, a cut-off point can be selected. For example, a simple way to identify a cut-off point is to array the measurements from the single time point for all subjects from high to low. The value residing at the upper or lower 95$^{th}$ percentile of the array of values can then be used as a cut-off point. Or, for example, the mean of the test values plus or minus 1.96 standard deviations can serve as a cut-off point.

In some embodiments, the cut-off point can be identified as the 0.025 fractile (2.5%) bound of the central 0.95 (95%) reference interval calculated at the single time point. Factors such as within-subject variation can also be considered when determining the cut-off point between normal and delayed gastric emptying. In some embodiments, the 95% level of diagnostic efficiency may be used, while in other embodiments, the diagnostic efficiency level chosen could be set lower at the 90%, 85% or 80% level, for example. In some embodiments, the single-point gastric emptying test can be used to identify a test result as normal, delayed, or borderline or perhaps as normal, accelerated, or boderline. Methods for identifying the cut off points for such zones are described in U.S. Pat. Pub. No. 2008-0281166, the disclosure of which is hereby incorporated by reference.

If the single-point breath test result is abnormal, a clinician diagnoses the subject as having delayed (or accelerated) gastric emptying. The clinician can then perform additional tests to determine the cause of the disorder and/or administer a treatment. After additional tests and treatment, a separate follow-up single-point breath test can be performed to obtain a post-treatment result. A clinician can then compare the post-treatment result with the original result, to determine whether the disorder is improving. In such cases, the same single-point breath test is first used as a diagnostic health test and then is later used to monitor treatment results.

The invention also provides a method for determining a special time window and/or a single time point for use in a single-point breath test. A gastric emptying breath test can be performed on a series of normal subjects to obtain breath test measurements at a series of time points. The normal subjects can be subjects that have previously obtained a normal gastric emptying test result. The same gastric emptying breath test, which includes the same test meal and the same test conditions, is also performed on a series of delayed subjects (or accelerated subjects) to obtain breath test measurements at the same series of time points. The delayed subjects (or accelerated subjects) can be subjects that have previously obtained a delayed or accelerated gastric emptying test result. The results of the breath test measurements between normal and the delayed subjects (or between normal and accelerated subjects) can be compared for each time point. The time window showing the sufficient measurement difference between normal and delayed subjects (or between normal and accelerated subjects) may be selected as the special time window from which a single time point can be selected. In some cases, the sufficient average measurement difference between normal and delayed subjects is at least about 10 kPCD and in some cases can be at least about 20 kPCD or at least about 30 kPCD. Likewise, in some cases the sufficient measurement difference between normal and accelerated subjects is at least about 10 kPCD and in some cases can be at least about 20 kPCD or at least about 30 kPCD.

In certain embodiments, the selected single time point can then be confirmed by statistical analysis. For example, one can calculate a 95% confidence interval around the mean value of healthy subjects at the selected single time point and calculate a 95% confidence interval around the mean value of the abnormal subjects at the same selected single time point. Non-overlapping confidence intervals between the normal and the abnormal subjects provides statistically clear evidence of frank separation. Hence, if the selected single time point displays a maximum average difference between normal and abnormal subjects and has non-overlapping 95% confidence intervals, that single time point can be used in a single-point breath test.

Additionally, the selected single time point can be confirmed by evaluating the diagnostic precision of that single time point. For example, the single time point's diagnostic precision can be confirmed by comparing the diagnostic performance of the breath test (e.g., sensitivity, specificity, concordance, NPV and PPV) at that single time point to the gold standard scintigraphy method at the same time point. The single time point's diagnostic precision can be also confirmed by comparing the diagnostic performance of the breath test at that single time point to a multi-point breath test over multiple time points.

Applicant performed both statistical analyses and diagnostic precision evaluations on several different time points from 0 to 240 minutes and discovered that for diagnosing delayed gastric empty, the time window that shows excellent diagnostic precision is between about 90 and about 150 minutes. Also, for diagnosing rapid gastric emptying, the time window is between about 30 and about 90 minutes. Such analyses and evaluations are discussed in the experimental section below.

EXPERIMENTAL

Example 1

Applicant performed the experiment of Example 1 to establish a diagnostically efficacious dose of $^{13}C$ for a single-point breath test. A dose is considered a diagnostically efficacious dose if it is sufficient to identify grossly delayed gastric emptying subjects (it must have sufficient signal above baseline noise) and to clearly and reliably discriminate between normal and abnormal (delayed or accelerated) subjects.

A test administrator performed breath testing on ten normal subjects and ten delayed subjects at different dose levels. The test meals included $^{13}C$-labeled *Spirulina platensis* incorporated into rehydrated lyophilized whole eggs. The test meals each had $^{13}C$-labeled *Spirulina platensis* in doses ranging from 20 to 80 mg of $^{13}C$. The test administrator tested each of the ten normal subjects and each of the ten delayed subjects at each dose level. Applicant found that excellent average separation occurred between the measurements of the normal and delayed subjects for all doses, with the maximum separation occurring during the time window of from about 90 to about 150 minutes.

The measurements for the 20 mg dose are shown in FIG. 1. The vertical bars extending above and below each point represent the 95% confidence interval. FIG. 1 shows that there was excellent average separation between the ten normal and the ten delayed subjects even at the low dose of 20 mg $^{13}C$, with the maximum separation occurring at between about 90 to about 150 minutes. Based on the results of Example 1, Applicant determined that a 20 to 80 mg $^{13}C$ dose can be used in the test meal.

Example 2

Applicant performed the experiment of Example 2 to determine a time window wherein a sufficient measurement difference occurs between normal and delayed subjects for a 43 mg $^{13}C$ test meal. A test administrator supplied a 43 mg $^{13}C$ test meal to five normal and two delayed subjects. The test administrator supplied the 43 mg $^{13}C$ dose into the test meal by approximately 100 mg of $^{13}C$-*Spirulina platensis* into the test meal, the $^{13}C$-*Spirulina* having approximately 43% by weight $^{13}C$. The test administrator then collected breath samples from each subject every 15 minutes and generated a measurement for those samples. FIG. 2 shows the measurements for each subject as kPCD versus time. The measurements confirm that excellent separation or measurement differences occurred between the breath test results for normal and delayed subjects during a time window of between about 90 minutes and about 150 minutes from time zero. Specifically, the 90 minute time point shows an average measurement difference of about 26 kPCD, the 100 minute time point shows a measurement difference of about 31 kPCD, the 110 minute time point shows a separation of about 34 kPCD, the 120 minute time point shows a separation of about 38 kPCD, the 130 minute time point shows a separation of about 38 kPCD, the 140 minute time point shows a separation of about 40 kPCD and the 150 minute time point shows a separation of about 40 kPCD.

Example 3

Applicant conducted the experiment of Example 3 to determine whether the time window of between about 90 minutes and about 150 minutes coincides with a time period of active emptying as measured by the gold standard method of scintigraphy. In Example 3, 30 healthy subjects ingested a dual labeled test meal, which included both $^{13}C$-labeled *Spirulina platensis* with 43 mg $^{13}C$ and 0.5 m Ci $^{99m}Tc$ sulphur colloid. A test administrator then performed scintigraphy to determine the fraction of the test meal emptied over a 4 hour period for each test subject. The results are shown graphically in FIG. 3 and the data is tabulated in Table 1 below.

TABLE 1

Mean Scintigraphic Fraction of Test Meal Emptied (N = 30 healthy subjects)

| | Measurement Time (Minutes) | | | | | | |
|---|---|---|---|---|---|---|---|
| | 0 | 45 | 90 | 120 | 150 | 180 | 240 |
| % Test Meal Emptied | 0 | 34 | 66 | 82 | 91 | 96 | 99 |

FIG. 3 and Table 1 show that the time window of between about 90 minutes and about 150 minutes indeed coincides with a period of active emptying of the test meal from the stomach as measured by scintigraphy. Also, at the 180 minute and 240 minute time points (at the end of the emptying cycle), the test meal is approaching complete emptying and the residuals of the test meal are asymptotic (approaching zero) in nature as is characteristically associated with gastric emptying.

Example 4

Example 4 demonstrates that the use of a 240 minute single time point is not favorable for use in the single-point breath test. In scintigraphy, a finding of greater than 10% of a test meal retained at 240 minutes is a classic scintigraphic diagnostic time point for diagnosing delayed emptying. However, in breath testing, the diagnostic signal ($^{13}CO_2$ excretion) is produced as a result of a multi-compartment process that goes beyond the stomach and therefore the response signal is delayed. As a result, one cannot simply extrapolate the idea of a single-point diagnostic test at the end of the emptying cycle from the scintigraphic model to a breath test, as is demonstrated in this Example 4.

A normal healthy subject ingested a test meal including $^{13}C$-labeled *Spirulina platensis* with 43 mg $^{13}C$. A different subject having delayed gastric emptying also ingested the same test meal. The results are shown in FIG. 4. The line with the data points indicated by an x shows measurements for the normal subject, while the line with the data points indicated by a diamond shows measurements for the delayed subject. The lines with data points indicated by a solid dot shows upper and lower reference range limits (95% confidence intervals) at each respective measurement time, which was derived separately as described in Example 5 below. Generally, if a breath test measurement falls within the upper and lower limits of the reference range, the measurement yields a normal test result and if the measurement falls outside the reference ranges, it yields a delayed result if below the lower limit s (and an accelerated result if above the upper limit).

With scintigraphy, measurements obtained on normal and delayed subjects at the 240 minute time point cannot reside in the same reference range. That is, if greater than 10% of the meal is still retained in the stomach at 240 minutes, the subject is classified as having delayed gastric emptying. If the stomach contains less than 10% of the meal at 240 minutes, the subject is classified as normal. Simply, a subject either does or does not have 10% or more of the test meal in his stomach at 240 minutes.

With breath testing, using a dose of 100 mg $^{13}C$-*Spirulina* and the lyophilized egg meal, healthy subjects who have consumed the test meal reach peak excretion of $^{13}CO_2$ (kPCD), on average, at about 150 minutes and then begin to decline as can be seen by observing the reference range limits in FIG. 4. Additionally, FIG. 4 shows with that breath testing, at later measurement times, the $^{13}CO_2$ excretion curve for the normal subject is declining while the $^{13}CO_2$ excretion curve for the delayed subject is still rising due to the slow exit of the meal from the stomach of the subject having delayed gastric emptying. At the 240 minute time point, the normal subject and delayed subject's curves coincidentally converge. In fact, the delayed subject has a measurement at the 240 minute time point that falls within the upper and lower reference range limits. As such, at the 240 minute time point, the delayed subject's measurement would yield a normal result, which would be considered a false result by the gold standard of scintigraphy.

Example 4 demonstrates that with breath testing, measurements from time points beyond 150 minutes show poor diagnostic discrimination between normal and delayed subjects. Thus one cannot simply select a later single time point for use in a single-point breath test. Applicant has specifically found that for a test meal containing $^{13}C$-labeled *Spirulina platensis* with 43 mg $^{13}C$, the appropriate time window to select a single time point from is between about 90 minutes and about 150 minutes. Hence, single-point measurements at later time points beyond 150 minutes using this test meal are problematic and can be diagnostically erroneous.

Example 5

Applicant performed the experiments in Example 5 to select reference ranges that can be used in a single-point breath test. A test administrator supplied a cohort of 60 healthy subjects with a test meal including $^{13}C$-labeled *Spirulina platensis* with 43 mg $^{13}C$. The test administrator obtained breath test measurements on each subject at time points 45, 90, 120, 150, and 180 minutes. From this data, Applicant calculated a 95% reference interval at each time point (N=60) to establish a breath test normal range. Applicant used the lower end of the 95% kPCD reference interval for each time point as the cut-off point (COP) to demarcate normal from delayed rates of gastric emptying. The subject values and reference range limits used in FIG. 4 are based on this data (N=60) at each time point.

Additionally, a test administrator supplied a cohort of 30 normal healthy subjects with a dual labeled test meal, which included both $^{13}C$-labeled *Spirulina platensis* with 43 mg $^{13}C$ and 0.5 m Ci $^{99m}Tc$ sulphur colloid. The test administrator then performed both scintigraphy and breath testing on each subject to collect the fraction of test meal emptied and kPCD measurements for each time point. From this data, at each time point, Applicant calculated a 95% reference interval to establish a scintigraphic normal range. Applicant also used the lower end of the 95% fraction emptied reference interval as the cut-off point (COP) to demarcate normal from slow rates of gastric emptying by scintigraphy. Hence, Applicant established normal reference ranges for each respective method at each time point.

The breath test and scintigraphic normal ranges for each time point are shown in Table 2 below. These ranges can be used to diagnose a subject as normal, delayed, or accelerated. For example, using the 90 minute measurement time as an example, a subject having a breath testing result<33.1 kPCD or a scintigraphic result<49.4% emptied would be classified as delayed. A subject having values above the upper limit of each range would be classified as accelerated.

TABLE 2

Reference Ranges

| Measurement Time (minutes) | GEBT (kPCD) | Scintigraphy (% meal emptied) |
|---|---|---|
| 45 | 12.9-32.9 | 18.1-50.5 |
| 90 | 33.1-63.2 | 49.4-80.9 |
| 120 | 44.2-72.5 | 67.8-95.1 |
| 150 | 49.3-74.5 | 77.4-100 |
| 180 | 46.5-70.5 | 87.5-100 |

Example 6

In Example 6, Applicant analyzed data from a previous study to identify single time points that have good diagnostic performance statistics. This previous study is described in Szarka L, Camilleri M, Vella A, et al. *A Stable Isotope Breath Test with a Standard Meal for Abnormal Gastric Emptying of Solids in the Clinic and in Research*. Clin Gastroenterol H. 2008; 8: 635-643. In the Szarka study, the reported cohort size was 129 subjects. In Example 6, however, Applicant excluded 14 subjects due to minor clinical protocol violations, such that the remaining cohort included 115 total subjects. Also, in the Szarka study, the test meal was a dual labeled test meal that included both $^{13}$C-labeled *Spirulina platensis* with 43 mg $^{13}$C and 0.5 m Ci $^{99m}$Tc sulphur colloid.

Applicant used breath test and scintigraphy measurements from the Szarka study at each time point (45 minutes, 90 minutes, 120 minutes, 150 minutes, 180 minutes and 240 minutes) to diagnose each subject as normal or delayed using the applicable cut off points calculated in Table 2 above. Applicant then compared the breath testing diagnosis of each subject at each time point to the scintigraphy diagnosis. For purposes of this analysis, Applicant considered the scintigraphy results as the true results, or the gold standard. Applicant classified each subject's breath test diagnosis, with reference to the scintigraphic diagnosis, as a true positive (TP), true negative (TN), false positive (FP) or false negative (FN). Applicant next compared the diagnostic performance characteristics of the breath test to scintigraphy at each time point by using standard calculations for sensitivity, specificity, concordance, negative predictive value (NPV) and positive predictive value (PPV). These results are shown in Table 3 below.

TABLE 3

Breath Test Performance Statistics by Time Point

| Classification Summary (N = 115) | Measurement Time (from end of test meal consumption) | | | | | |
|---|---|---|---|---|---|---|
| | 45 Min | 90 Min | 120 Min | 150 Min | 180 Min | 240 Min |
| TP—True Positives | 16 | 41 | 48 | 41 | 29 | 15 |
| TN—True Negatives | 84 | 54 | 45 | 49 | 56 | 62 |
| FP—False Positives | 6 | 11 | 13 | 13 | 8 | 7 |
| FN—False Negatives | 9 | 9 | 9 | 12 | 22 | 31 |
| Performance Statistics | | | | | | |
| Sensitivity | 64.0 | 82.0 | 84.2 | 77.4 | 56.9 | 32.6 |
| Specificity | 93.3 | 83.1 | 77.6 | 79.0 | 87.5 | 89.9 |
| Concordance | 87.0 | 82.6 | 80.9 | 78.3 | 73.9 | 67.0 |
| PPV (Positive Predictive Value) | 72.7 | 78.9 | 78.7 | 75.9 | 78.4 | 68.1 |
| NPV (Negative Predictive Value) | 90.3 | 85.7 | 83.3 | 80.3 | 71.8 | 66.7 |

The diagnostic performance statistics of the breath test versus scintigraphy were then evaluated across each time point to identify the time points at which the performance statistics were the best. On average, across all performance measures, the 90, 120 and 150 minute time points displayed the best performance characteristics.

The lower sensitivity observed at the 180 and 240 minute time points in Table 3 arises from the fact that modestly delayed test subjects have $^{13}CO_2$ excretion curves that finally begin rising at later time points beyond 150 minutes, at which times the breath test measurements may fall within the normal reference range established for the 180 or 240 minute time points. Again, this phenomenon is shown in FIG. 4. If this occurs, without consideration of breath test measurements obtained at earlier time points, the subject would be erroneously classified as normal if the later time points were used as the only time point for a single-point breath test.

Further, if the test subject is actually classified as having delayed emptying by scintigraphy by using a single breath test measurement one of these later time points, then, compared to scintigraphy, the subject must be classified as a false negative (FN) by breath testing. Because diagnostic sensitivity is defined by the equation sensitivity=(true positives/(true positives+false negatives), then the greater number of breath test false negatives (FN) at later time points, the lower the sensitivity. Hence, Applicant discovered that single time points within the about 90 minutes to about 150 minutes time window are more diagnostically accurate than time points beyond 150 minutes.

It should be understood that the optimal time point for a single-point breath test, as the time point having the best performance characteristics, may depend upon the intended use of the test. For example, if the single-point breath test is for use in population screening, the time point with the best specificity and NPV might be the optimal time point. If the test is used for diagnosing delayed emptying in a clinic setting, the time point having the highest sensitivity may be the optimal time point. Finally, if the group of subjects being tested had an approximately even distribution between delayed and normal rates of gastric emptying, the time point having the highest overall diagnostic concordance might be the optimal time point for a single-point breath test. In this case, however, as can be seen from Table 3, on average, across all performance statistics, the 90 minute time point had the best performance statistics. This indicates that the 90 minute time point was the optimal time point, resulting in the highest values for both sensitivity and specificity. Applicant therefore selected the 90 minute time point as an optimal time point for the single-point breath test, although other time points within the range of about 90 minutes to about 150 minutes are also very good.

Example 7

Applicant next evaluated the 90 minute time point to verify that it is not diagnostically inferior to a multi-point breath test. It should be recognized, however, that because a single-point breath test may take 90 minutes, while a multi-point test can take 240 minutes and requires multiple samplings, a tradeoff in diagnostic performance may be acceptable. However, if a loss in diagnostic performance is significant for the single-point breath test as compared to the multi-point test, the tradeoff would not be acceptable. For example, it is unlikely that a single-point breath test would be utilized with 60% sensitivity if the multi-point test performs at 85% sensitivity.

Using the breath test and scintigraphic measurements obtained from the cohort of 115 subjects from the Szarka study, Applicant evaluated the relationship of kPCD to Scint_FE at the 90 minute time point. The results are shown in FIG. 5, which is an x-y scatter plot displaying the relationship between breath results and the scintigraphic results. The ascending straight line in the plot represents the best fit of the data using a simple linear regression model. FIG. 5 shows that on average breath measurements are proportional to scintigraphic measurements at the 90 minute time point. This linear, proportional relationship also holds true at 120 and 150 minutes.

Applicant also determined that the 90 minute time point had a correlation coefficient (r) of 0.84. The correlation coefficients for the 120 and 150 time points were similar at 0.85 and 0.84, respectively, showing that the relationship of breath test to scintigraphic measurements remains consistent throughout the time window of from about 90 minutes to about 150 minutes. Applicant also determined that the 90 minute time point had a coefficient of determination ($r^2$) of 0.71, which indicates that about 71% of the observed variation in breath test results could be attributed to a linear relationship between breath testing and scintigraphy (that is, natural variability as measured by scintigraphy). The remaining variability was likely due to the collective variation in the rates of processes that follow gastric emptying for breath testing (such as pancreatic function, intestinal absorption, portal transport, hepatic metabolism and pulmonary gas exchange) that also affect breath test results. Thus, Example 7 shows that at 90, 120 and 150 minute time points, the breath test measurements had a correlation coefficient of at least 0.80 compared to scintigraphy measurements.

Example 8

In Example 8, Applicant used multiple linear regression (MLR) methods (such as those described in the Szarka paper) to help verify the best time point for the single-point breath test. As reported in Example 7, breath test measurements and scintigraphy measurements are highly correlated at the 90 minute, 120 minute and 150 minute time points. The favorable correlation of the two independent test method metrics in both normal subjects and delayed subjects facilitates using the MLR methods described below.

As discussed above, the traditional gastric emptying measurement metric is the fraction of test meal emptied at time t, as determined by scintigraphy (Scint_FE)$_t$. Applicant converted the breath test measurements (kPCD) into a measurement equivalent to fraction of test meal emptied at time t (BT_FE$_{(t)}$) using the MLR method.

Applicant used breath test and scintigraphic measurements from the cohort of 115 subjects to derive appropriate MLR equations for each time point. The MLR modeling is appropriate and reliable because the two independent test method metrics are highly correlated, the subjects spanned gastric emptying rates across normal and abnormal (very slow to very fast) and the distribution of delayed and non-delayed subjects was about even (50%).

Applicant also tested 50 normal subjects, independent of the 115 cohort subjects from the Szarka study, in the same manner as the 115 cohort subjects. Using the measurements obtained from these 50 normal subjects, Applicant calculated the 95% reference range and cut off points, at each time point, for directly measured Scint_FE$_{(t)}$. Applicant also converted the kPCD values for each normal subject to BT_FE$_{(t)}$ values at each time point using the applicable MLR equation for each time point. Next, Applicant calculated the BT_FE$_{(t)}$ reference ranges for each time point. This allowed Applicant to directly compare each subject's diagnostic classification by scintigraphy (Scint_FE$_{(t)}$) to classification by breath testing (BT_FE$_{(t)}$). The reference ranges and the performance characteristics of the single-point breath test versus scintigraphy using these like metrics at each time point (out to 180 minutes) are reported in Tables 4 and 5, below. The lower end of the reference ranges in Table 4 served as the diagnostic cut off point for each respective test method.

TABLE 4

| | Reference Ranges | | | | |
|---|---|---|---|---|---|
| Test | 45 Minutes | 90 Minutes | 120 Minutes | 150 Minutes | 180 Minutes |
| Scint_FE$_{(t)}$ | 0.183-0.529 | 0.490-0.835 | 0.645-0.948 | 0.750-0.998 | 0.850-1.000 |
| BT_FE$_{(t)}$ | 0.213-0.485 | 0.461-0.908 | 0.610-1.000 | 0.699-1.000 | 0.763-1.000 |

TABLE 5

Performance Characteristics Using BT_FE$_{(t)}$ and Scint_FE$_{(t)}$ Metrics

| | 45 Minutes | 90 Minutes | 120 Minutes | 150 Minutes | 180 Minutes |
|---|---|---|---|---|---|
| Classification | | | | | |
| TP | 16 | 42 | 43 | 38 | 29 |
| TN | 81 | 59 | 54 | 62 | 66 |
| FP | 8 | 6 | 9 | 3 | 4 |
| FN | 10 | 8 | 9 | 12 | 16 |
| Performance Statistic | | | | | |
| Sensitivity | 61.5 | 84.0 | 82.7 | 76.0 | 64.4 |
| Specificity | 91.0 | 90.8 | 85.7 | 95.4 | 94.3 |
| Concordance | 84.3 | 87.8 | 84.3 | 87.0 | 82.6 |
| PPV | 66.7 | 87.5 | 82.7 | 92.7 | 87.9 |
| NPV | 89.0 | 88.1 | 85.7 | 83.8 | 80.5 |

Once again, on average, across all measures, the 90 and 120 minute time points displayed the best performance. The 150 minute measurement time was also comparable to the 90 and 120 minute measurement times. Thus, using the calculated metric BT_FE$_{(t)}$, Applicant again verified that the ideal time window is between about 90 minutes and about 150 minutes. Also, the performance statistics across this time window were slightly better than those observed using BT_kPCD. Using the BT_FE(t) metric, Applicant again selected the 90 minute time point as an optimal single time point for the single-point breath test.

Example 9

Another metric utilized in scintigraphy is the "half-emptying time", commonly referred to as the scintigraphic t ½ (Scint_t ½). The half-emptying time is the time at which a subject empties half of the standardized test meal from the stomach. In scintigraphy, the direct measurement of the fraction emptied at each time point, $Scint\_FE_{(t)}$, is reported at 45, 90, 120, 150, 180 and 240 minute time points. Using this data, one calculates the Scint_t ½ using linear interpolation between the two time points between which the value of $Scint\_FE_{(t)}$ of 0.5 (50%) falls. Calculation of the breath test half-emptying time (BT_t %) is analogous to calculation of Scint_t ½. Thus, one can also calculate BT_t ½ using linear interpolation between the two measurement times between which the $BT\_FE_{(t)}$ value of 0.5 (50%) falls.

In Example 9 Applicant determined the reference ranges for Scint_t ½ and BT_t ½ from the measurements of the 50 normal subjects of Example 8, using the 95% reference range as described above. Using the MLR approach as described above with regard to Example 8, Applicant compared the breath test measurements obtained in Example 6 to scintigraphy using the t ½ metric. Using linear interpolation, Applicant used the respective $Scint\_FE_{(t)}$ and $BT\_FE_{(t)}$ values across all time points from Example 8 to generate t ½ values. Applicant also calculated the respective 95% t ½ reference ranges from the Scint_t ½ and BT_t ½ values obtained from the 50 healthy subjects with the upper end of the ranges serving as the diagnostic t ½ cut off point. Because of the nature of the t ½ metric, increasing t ½ values actually represent slower rates of gastric emptying. Hence, the upper limit of the t ½ reference range is used as the cut-off point (COP) to demarcate delayed from normal gastric emptying. (Note: that the MLR equations are appropriate and applicable is verified by the fact the mean scintigraphic t ½ value of the 50 healthy subjects was 68 minutes and the mean BT_t ½ value was 69 minutes—virtually identical).

Using linear interpolation, Applicant then calculated the Scint_t ½ and BT_t ½ values for each of the 115 subjects from the Szarka study. Applicant then compared each subject's diagnostic classification by breath test (BT_t ½) to their classification by scintigraphy (Scint_t ½). The reference ranges using the t ½ metric are reported below in Table 5 and the performance characteristics of the BT_t ½ versus scintigraphy t ½ are reported below in Table 6.

TABLE 5

| | t½ Reference Ranges | |
|---|---|---|
| Test Method | Scint_$t_{1/2}$ (Minutes) | BT_$t_{1/2}$ (Minutes) |
| Reference Range | 43.1-91.6 | 46.5-97.5 |

TABLE 6

Breath Test Performance Characteristics vs. Scintigraphy Using t½ Metrics

| | BT_t½ vs. Scint._t½ |
|---|---|
| Classification | |
| TP | 43 |
| TN | 59 |
| FP | 6 |
| FN | 7 |
| Statistical Performance | |
| Sensitivity | 86.0 |
| Specificity | 90.8 |
| Concordance | 88.7 |
| PPV | 87.8 |
| NPV | 89.4 |

On a non-statistical basis, it appears that performance characteristics of breath test versus scintigraphy, when measured by using the MLR approach and t ½ metrics, are modestly better but comparable to the single-point breath test performance statistics at 90 minutes when using kPCD vs. fraction emptied metrics. A side by side comparison of the performance characteristics of a 90 minute single-point breath test measured in BT_kPCD, BT_FE, and BT_t ½ metrics as compared to scintigraphy are shown in Table 7 below.

TABLE 7

Comparison of Breath Test Performance Characteristics across Metrics

| | 90 Minute BT_kPCD Vs. Scint_FE | 90 Minute BT_FE vs. Scint_FE | BT_t½ vs. Scint._t½ |
|---|---|---|---|
| Classification & Statistics N = 115 | | | |
| TP | 41 | 42 | 43 |
| TN | 54 | 59 | 59 |
| FP | 11 | 6 | 6 |
| FN | 9 | 8 | 7 |
| Performance Statistic | | | |
| Sensitivity | 82.0 | 84.0 | 86.0 |
| Specificity | 83.1 | 90.8 | 90.8 |
| Concordance | 82.6 | 87.8 | 88.7 |
| PPV | 78.9 | 87.5 | 87.8 |
| NPV | 85.7 | 88.1 | 89.4 |

Example 9 shows that the BT_t ½ metric has excellent diagnostic performance characteristics as compared to the like metric of Scint_t ½ as determined using scintigraphy (both tests require using data from the multi-point test and conducting linear interpolation to calculate t ½) However, note that a single point test at 90, 120 and 150 measurement times demonstrates very comparable performance characteristics to the multi-point t ½ approach, especially at 90 minutes. As such, the preliminary selected 90 minute single-point breath test has comparable performance of the multi-point t ½ test.

Example 10

In Example 10, Applicant compared the performance of the single-point breath test to the performance of the multi-point test (t ½ metric) using the Fisher Exact Test (FET). Applicant also compared the performance of the breath test BT_$t_{1/2}$ metric to the performance of the calculated breath test fraction emptied metric BT_FE$_{(t)}$. Applicant used data from Examples 8 and 9 above to make this comparison. Applicant compared each of the measurement times for the single-point breath test to the multi-point test (BT_t ½).

Applicant performed all FET calculations using version 4.01 of StatExact software. The results of the comparison are shown in Table 8 below. In the FET, the null hypothesis states that two proportions are equal, i.e., Ho: $p_1=p_2$. Thus, a probability of the FET less than 0.05 indicates a significant difference between the proportions at the 0.05 level of significance. There was no statistically significant difference in the diagnostic performance of the single-point breath test, expressed in BT_$t_{1/2}$ metric, versus the breath test's multi-point diagnostic performance, using BT_$t_{1/2}$ metric, at measurement times of 90, 120 and 150 minutes. However, the FET probability values of less than 0.05 for the 45 minute and 180 minute single-point breath test results (for the sensitivity comparison) indicate that the difference in performance was statistically significant at these measurement times. The single-point breath test at the 90, 120 or 150 minute measurement times is therefore as good at diagnosing delayed emptying as the multi-point breath test using BT_t ½ or Scintigraphic t ½ metrics.

TABLE 8

Fisher Exact Test Statistics: BT_$t_{1/2}$ metric versus BT_FE$_{(t)}$

| Classification & Statistics N = 115 | 45 Min BT_FE vs. Scint_FE | 90 Min BT_FE vs. Scint_FE | 120 Min BT_FE vs. Scint_FE | 150 Min BT_FE vs. Scint_FE | 180 Min BT_FE vs. Scint_FE | $t_{1/2}$ BT t½ vs. Scint. t½ |
|---|---|---|---|---|---|---|
| TP | 16 | 42 | 43 | 38 | 29 | 43 |
| TN | 81 | 59 | 54 | 62 | 66 | 59 |
| FP | 8 | 6 | 9 | 3 | 4 | 6 |
| FN | 10 | 8 | 9 | 12 | 16 | 7 |
| Performance Characteristics | | | | | | |
| Sensitivity | 61.5 | 84.0 | 82.7 | 76.0 | 64.4 | 86.0 |
| Specificity | 91.0 | 90.8 | 85.7 | 95.4 | 94.3 | 90.8 |
| Concordance | 84.3 | 87.8 | 84.3 | 87.0 | 82.6 | 88.7 |
| PPV | 66.7 | 87.5 | 82.7 | 92.7 | 87.9 | 87.8 |
| NPV | 89.0 | 88.1 | 85.7 | 83.8 | 80.5 | 89.4 |
| Fisher Exact Test Probabilities | | | | | | |
| Sensitivity | 0.0213 | 1.0000 | 0.7870 | 0.3080 | 0.0174 | |
| Specificity | 1.0000 | 1.0000 | 0.4204 | 0.4920 | 0.5207 | |
| Concordance | 0.4403 | 1.0000 | 0.4403 | 0.8406 | 0.2589 | |
| PPV | 0.0547 | 1.0000 | 0.5799 | 0.5018 | 1.0000 | |
| NPV | 1.0000 | 1.0000 | 0.5991 | 0.4594 | 0.1729 | |

Example 11

Applicant performed the experiment of Example 11 to determine a time window wherein a sufficient separation of measurement difference occurs between normal and accelerated subjects for a 43 mg $^{13}$C test meal. In FIG. 6, the bottom line with data points represented as circles shows the mean breath test measurements for delayed subjects identified by the Szarka study. The top line with data points represented as triangles shows the mean breath test measurements for accelerated subjects identified by the Szarka study. The middle line with data points represented as squares shows the mean breath test measurements from the cohort of 60 subjects used to establish normal reference ranges from Example 5.

FIG. 6 shows that excellent separation or sufficient measurement differences occurred between the breath test results for normal and accelerated subjects during a time window of between about 30 and 90 minutes from time zero. More specifically too, both the 45 minute time point and the 90 minute time point show a measurement difference of about 12 kPCD.

What is claimed is:

1. A breath test method for identifying delayed gastric emptying, comprising:
    supplying a subject with a solid breath test meal having a *Spirulina platensis* $^{13}$C label, wherein the solid breath test meal has a caloric content of between about 200 and about 400 kilocalories;
    collecting a post-meal breath sample of the subject, wherein the collecting the post-meal breath sample consists of collecting only a single breath sample of the subject at only a single 90 minute time point after the subject consumes the solid breath test meal;
    providing a device configured to measure a ratio of $^{13}CO_2/^{12}CO_2$ in the single breath sample;
    quantitatively measuring the ratio of $^{13}CO_2/^{12}CO_2$ in the single breath sample using the device;
    generating a gastric emptying measurement from the single breath sample; and
    identifying whether the subject has delayed gastric emptying based on the gastric emptying measurement, wherein the step of identifying whether the subject has delayed gastric emptying involves classifying the subject based on a dichotomous classification system such that the subject is classified as having either normal gastric emptying or delayed gastric emptying.

2. The breath test method of claim 1 wherein the $^{13}$C label is present in the solid breath test meal in a dose that statistically discriminates between normal subjects having normal gastric emptying and delayed subjects having delayed gastric emptying.

3. The breath test method of claim 1 wherein the $^{13}$C label is present in the solid breath test meal in a dose of between about 20 mg to about 80 mg.

4. The breath test method of claim 1 wherein the caloric content of the solid breath test meal is about 400 kilocalories.

5. The breath test method of claim 1 wherein the device is a mass spectrometer or an infrared spectrometer.

6. The breath test method of claim 1 wherein the $^{13}$C label is present in the solid breath test meal in a dose of between about 40 mg to about 50 mg.

7. The breath test method of claim 1 wherein the solid breath test meal comprises food components derived from lyophilized food components.

8. The breath test method of claim 1 wherein the solid breath test meal further comprises lyophilized whole eggs.

9. The breath test method of claim 1 wherein the solid breath test meal further comprises scrambled eggs.

10. The breath test method of claim 1 wherein the solid breath test meal further comprises bread or crackers.

11. The breath test method of claim 1 wherein after determining that the subject has delayed gastric emptying, the method further comprises administering a treatment to the subject to treat the delayed gastric emptying.

\* \* \* \* \*